(12) United States Patent
Isomura et al.

(10) Patent No.: US 7,036,352 B2
(45) Date of Patent: May 2, 2006

(54) GAS SENSOR

(75) Inventors: Hiroshi Isomura, Aichi (JP); Shoji Akatsuka, Kasugai (JP); Osamu Shinkai, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/879,727

(22) Filed: Jun. 30, 2004

(65) Prior Publication Data

US 2005/0016257 A1 Jan. 27, 2005

(30) Foreign Application Priority Data

Jul. 4, 2003 (JP) .................... P. 2003-192263

(51) Int. Cl.
*G01N 27/26* (2006.01)
(52) U.S. Cl. ..................... 73/23.2; 204/428
(58) Field of Classification Search ............... 73/23.2; 204/428
See application file for complete search history.

(56) References Cited

U.S. PATENT DOCUMENTS

| 5,762,771 | A | * | 6/1998 | Yamada et al. | ............. 204/428 |
| 5,874,664 | A | * | 2/1999 | Watanabe et al. | ........... 73/23.32 |
| 6,178,806 | B1 | * | 1/2001 | Watanabe et al. | ........... 73/23.32 |
| 6,258,234 | B1 | * | 7/2001 | Watanabe et al. | ........... 204/424 |
| 6,279,376 | B1 | * | 8/2001 | Yamada et al. | ............. 73/23.2 |
| 6,348,141 | B1 | | 2/2002 | Kato et al. | |
| 6,548,023 | B1 | * | 4/2003 | Matsuo et al. | ................ 422/83 |
| 6,618,927 | B1 | * | 9/2003 | Tajima et al. | ................. 29/595 |
| 6,913,678 | B1 | * | 7/2005 | Yamada et al. | ............. 204/424 |
| 2001/0054552 | A1 | * | 12/2001 | Matsuo et al. | ............... 204/421 |
| 2002/0000033 | A1 | * | 1/2002 | Tajima et al. | .............. 29/592.1 |
| 2003/0074952 | A1 | | 4/2003 | Shirai | |
| 2003/0094368 | A1 | * | 5/2003 | Yamada et al. | ............. 204/431 |
| 2004/0007462 | A1 | * | 1/2004 | Hotta et al. | ................. 204/429 |

FOREIGN PATENT DOCUMENTS

| EP | 0 822 410 A2 | 2/1998 |
| EP | 1 139 098 A2 | 10/2001 |
| EP | 1 391 724 A1 | 2/2004 |
| EP | 1 494 023 A1 | 1/2005 |
| JP | 2000-171429 A | 6/2000 |
| JP | 2000-304719 A | 11/2000 |
| JP | 2002-162377 A | 6/2002 |

* cited by examiner

*Primary Examiner*—Hezron Williams
*Assistant Examiner*—Rodney Frank
(74) *Attorney, Agent, or Firm*—Sughrue Mion, PLLC

(57) ABSTRACT

A gas sensor comprising: a gas sensor element extending in an axial direction; a cylindrical metal shell enclosing said gas sensor element such that a leading end portion of said gas sensor element protrudes from its own leading end; and a protector fixed on said metal shell and covering said leading end portion of said gas sensor element, wherein said protector includes: a cylindrical outer cover portion fixed on said metal shell and having gas introducing apertures; and a cylindrical inner cover portion arranged on an inner side of said outer cover portion and having elastic portions being capable of being elastically deformed by a pushing force acting in an axial direction, and said inner cover portion is so clamped between said metal shell and said outer cover portion that said elastic portions are elastically deformed by said axial pushing force.

9 Claims, 4 Drawing Sheets

GAS SENSOR

FIELD OF THE INVENTION

The present invention relates to a gas sensor and, more particularly, to a gas sensor provided with a protector for covering such a portion of a gas sensor element having a bottomed cylindrical shape or a plate shape as will be exposed to an object gas to be measured.

BACKGROUND OF THE INVENTION

A gas sensor such as an oxygen sensor, a NOx sensor or an HC sensor is known in the prior art. This gas sensor is generally provided with a protector for covering and protecting such a leading end portion of a gas sensor element as will be exposed to the object gas such as an exhaust gas. Some protector is given a double structure by considering the responsibility of the sensor, the water resistance of the gas sensor element and so on. The gas sensor having the protector of such double structure is disclosed in JP-A-2002-162377, for example.

In this gas sensor, the protective tube (or protector) is composed of an outer protective tube (or outer cover portion) and an inner protective tube (or inner cover portion). Of these, the outer protective tube is welded and fixed at its trailing end portion to the outer circumference of the leading end edge of the metal shell. On the other hand, the inner protective tube is welded and fixed on the outer face of its leading end portion to the inner face of the leading end portion of the outer protective tube. In short, this protective tube is fixed to the metal shell such that its inner protective tube is fixed at its leading end portion to the outer protective tube and such that the outer protective tube is fixed at its trailing end portion to the metal shell.

In case this gas sensor is subjected to high vibrations for a long term, the welded portion between the inner protective tube and the outer protective tube may be broken. Then, the inner protective tube will seriously vibrate, when used, in the outer protective tube. Then, an abnormal noise is generated, or the gas sensor element may be broken, as the case may be. Moreover, the inner protective tube may move to exert adverse affects on the gas sensibility or responsibility of the sensor. In short, it cannot be said that the protective tube, especially its inner protective tube has satisfactory vibration resistance.

SUMMARY OF THE INVENTION

The invention has been conceived in view of the background thus far described, and has an object to provide a gas sensor having a protector excellent in vibration resistance.

According to an aspect of the invention, there is provided a gas sensor comprising: a gas sensor element extending in the axial direction; a cylindrical metal shell enclosing the gas sensor element such that the leading end portion of the gas sensor element protrudes from its own leading end; and a protector fixed on the metal shell and covering the leading end portion of the gas sensor element, wherein the protector includes: a cylindrical outer cover portion fixed on the metal shell and having gas introducing apertures; and a cylindrical inner cover portion arranged on the inner side of the outer cover portion and having such elastic portions as can be elastically deformed by a pushing force acting in the axial direction, and wherein the inner cover portion is so clamped between the metal shell and the outer cover portion that the elastic portions are elastically deformed by the axial pushing force.

According to the invention, the inner cover portion includes the elastic portions, which can be elastically deformed by the pushing force acting in the axial direction. Moreover, the inner cover portion is clamped in such a state between the metal shell and the outer cover portion that the elastic portions are elastically deformed. In this gas sensor, therefore, the inner cover portion keeps the state, in which it abuts against the metal shell and the outer cover portion, even if it is subjected to vibrations. Even in case the gas sensor is subjected to serious vibrations for a long time, therefore, the inner cover portion is prevented from being seriously vibrated in the outer cover portion.

Here, the inner cover portion including the elastic portions may take any shape if it can satisfy the aforementioned requirements. For example, elastic members of springs or the like are disposed on the leading end side or the trailing end side of the inner cover portion. Moreover, elastic members of springs are disposed at the axially intermediate portions of the inner cover portion. Alternatively, the inner cover portion may be provided with elastically deformable flange portions, as will be described hereinafter.

In the gas sensor, moreover, the inner cover portion may include an inner cylindrical portion enclosing the leading end portion of the gas sensor element, and the elastic portions may have flange portions protruding radially outward from the inner cylindrical portion and elastically deformed when pushed toward the leading end side in the axial direction by the metal shell to come into direct or indirect abutment against the flange portions.

According to the invention, the elastic portions of the inner cover portion include the flange portions protruding radially outward from the inner cylindrical portion. These flange portions are elastically deformed by the push of the metal shell. With this construction, the protector can be given a simple structure while having its vibration resistance improved.

Here, the flange portions may be molded integrally with or separately of the inner cylindrical portion, but the integral molding is preferred from the viewpoint of cost.

In the aforementioned gas sensor, moreover, the flange portions may be intermittent flange portions arranged intermittently in the circumferential direction.

According to the invention, the flange portions are the intermittent flange portions arranged intermittently in the circumferential direction. With this construction, the elastic deformations of the flange portions can be effectively caused to contribute to the lower cost.

In any of the aforementioned gas sensors, moreover, the inner cover portion may include leg portions protruding from the radially outer end portions of the flange portions and positioned at their own trailing ends closer to the trailing end side than the trailing end of the inner cylindrical portion so that they are pushed toward the leading end side in the axial direction when the leading end of the metal shell comes into abutment against themselves.

According to the invention, the flange portions, which can be elastically deformed while being clamped between the metal shell and the outer cover portion, are provided at their radially outer end portions with the leg portions protruding toward the trailing end in the axial direction and positioned at their own trailing ends closer to the trailing end side than the trailing end of the inner cylindrical portion so that they are pushed toward the leading end side in the axial direction when the leading end of the metal shell comes into abutment against themselves. With this construction, the flange portions are elastically deformed while being pushed by the metal shell through the leg portions so that the elastic deformation of the flange portions are stabilized. Especially if the flanged portions are formed into the aforementioned intermittent flange portions and if the leg portions are formed at the radially outer end portions, a space (or clearance) can be formed between the intermittent flange portions and the leading end of the metal shell so that the object gas introduced from the gas introducing apertures of the outer cover portion can be introduced through the intermittent flange portions and over the trailing end of the inner cylindrical portion into the inner cover portion. Therefore, it is possible to retain the vibration resistance of the protector, to simplify the structure of the protector and to construct the communication passage of the object gas easily. From the viewpoint of the molding procedure and the cost, the leg portions protruding the flange portions are preferably molded integrally with the inner cylindrical portion and the flange portions.

In any of the aforementioned gas sensors, moreover, the outer cover portion and the inner cover portion may be fixed to each other at their any portions.

According to the invention, the outer cover portion and the inner cover portion are fixed to each other at their any portions. Thus, it is possible to improve the vibration resistance of the inner cover portion better.

In the aforementioned gas sensor, moreover, the outer cover portion may include: an outer cylindrical portion fixed on the metal shell; and an outer bottom portion positioned closer to the leading end side than the outer cylindrical portion and having an outer leading end air vent hole, and the inner cover portion may also include: an inner cylindrical portion enclosing the leading end portion of the gas sensor element; and an inner bottom portion positioned closer to the leading end side than the inner cylindrical portion and having an inner leading end air vent hole communicating with the outer leading end air vent hole. The outer bottom portion and the inner bottom portion may also be fixed to each other.

By thus fixing the outer bottom portion having the outer leading end air vent hole and the inner bottom portion having the inner leading end air vent hole to each other, the outer cover portion and the inner cover portion can be stablly fixed to improve the vibration resistance of the inner cover portion better.

According to another aspect of the invention, there is provided a gas sensor comprising: a gas sensor element extending in the axial direction; a cylindrical metal shell enclosing the gas sensor element such that the leading end portion of the gas sensor element protrudes from its own leading end; and a protector fixed on the metal shell and covering the leading end portion of the gas sensor element, wherein the protector includes: a cylindrical outer cover portion fixed on the metal shell and having an outer cylindrical portion fixed on the metal shell and having gas introducing apertures, and an outer bottom portion positioned on the leading end side of the outer cylindrical portion and having an outer leading end air vent hole communicating with the outside; and a cylindrical inner cover portion arranged on the inner side of the outer cover portion and having an inner cylindrical portion enclosing the leading end portion of the gas sensor element, an inner bottom portion positioned on the leading end side of the inner cylindrical portion and having an inner leading end air vent hole communicating with the outer leading end air vent hole of the outer cover portion, intermittent flange portions protruding radially outward from the trailing ends of the inner cylindrical portion and arranged intermittently in the circumferential direction so that they can be elastically deformed by a pushing force acting in the axial direction, and leg portions protruding toward the trailing end in the axial direction from the radially outer end portions of the intermittent flange portions, and wherein the intermittent flange portions are elastically deformed by pushing the leg portions of the inner cover portion toward the leading end in the axial direction with the leading end of the metal shell, and by pushing at least a portion of the inner bottom portion of the inner cover portion toward the trailing end in the axial direction with at lest one portion of the outer bottom portion of the outer cover portion.

According to the invention, the inner cover portion includes: the intermittent flange portions, which protrude radially outward from the trailing end of the inner cylindrical portion and which are arranged intermittently in the circumferential direction so that they can be elastically deformed by the pushing force acting in the axial direction; and the leg portions which protrude toward the trailing end in the axial direction from the radially outer end portions of the intermittent flange portions. Moreover, the intermittent flange portions are elastically deformed by pushing the leg portions of the inner cover portion toward the leading end in the axial direction with the leading end of the metal shell, and by pushing at least a portion of the inner bottom portion of the inner cover portion toward the trailing end in the axial direction with at lest one portion of the outer bottom portion of the outer cover portion. In this gas sensor, therefore, the inner cover portion keeps the state, in which it abuts against the metal shell and the outer cover portion, so that the inner cover portion is prevented from being seriously vibrated in the outer cover portion. In addition, the structure of the protector can be simplified. Moreover, it is easy to construct the communication passage, which guides the object gas introduced from the gas introducing apertures of the outer cover portion, between the intermittent flange portions and over the trailing end of the inner cylindrical portion into the inner cover portion.

DETAILED DESCRIPTION OF THE INVENTION

An embodiment of the invention will be described with reference to the accompanying drawings.

Figure 1:
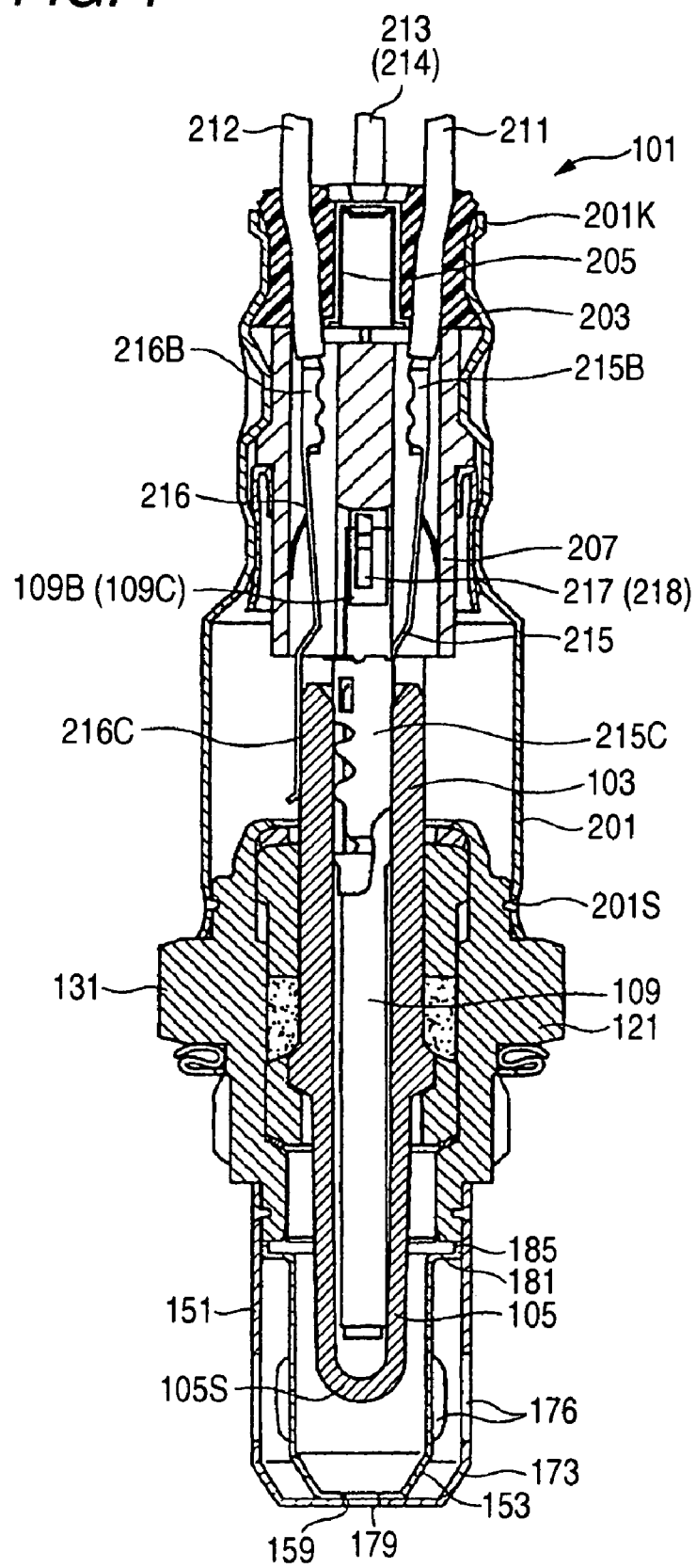
FIG. 1 is a sectional view showing a gas sensor according to an embodiment.
Figure 2:
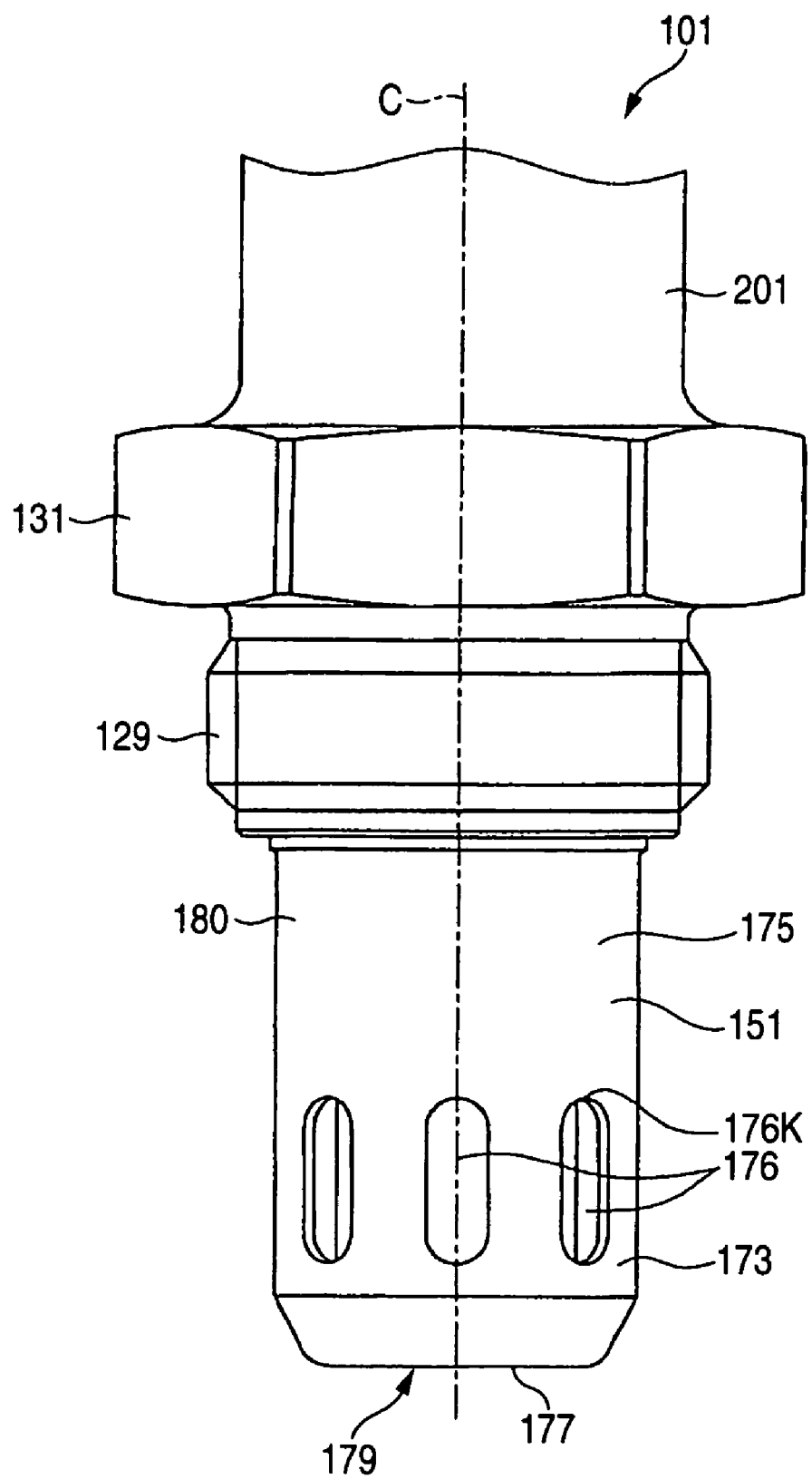
FIG. 2 is a top plan view of an essential portion of the gas sensor according to the embodiment.
Figure 3:
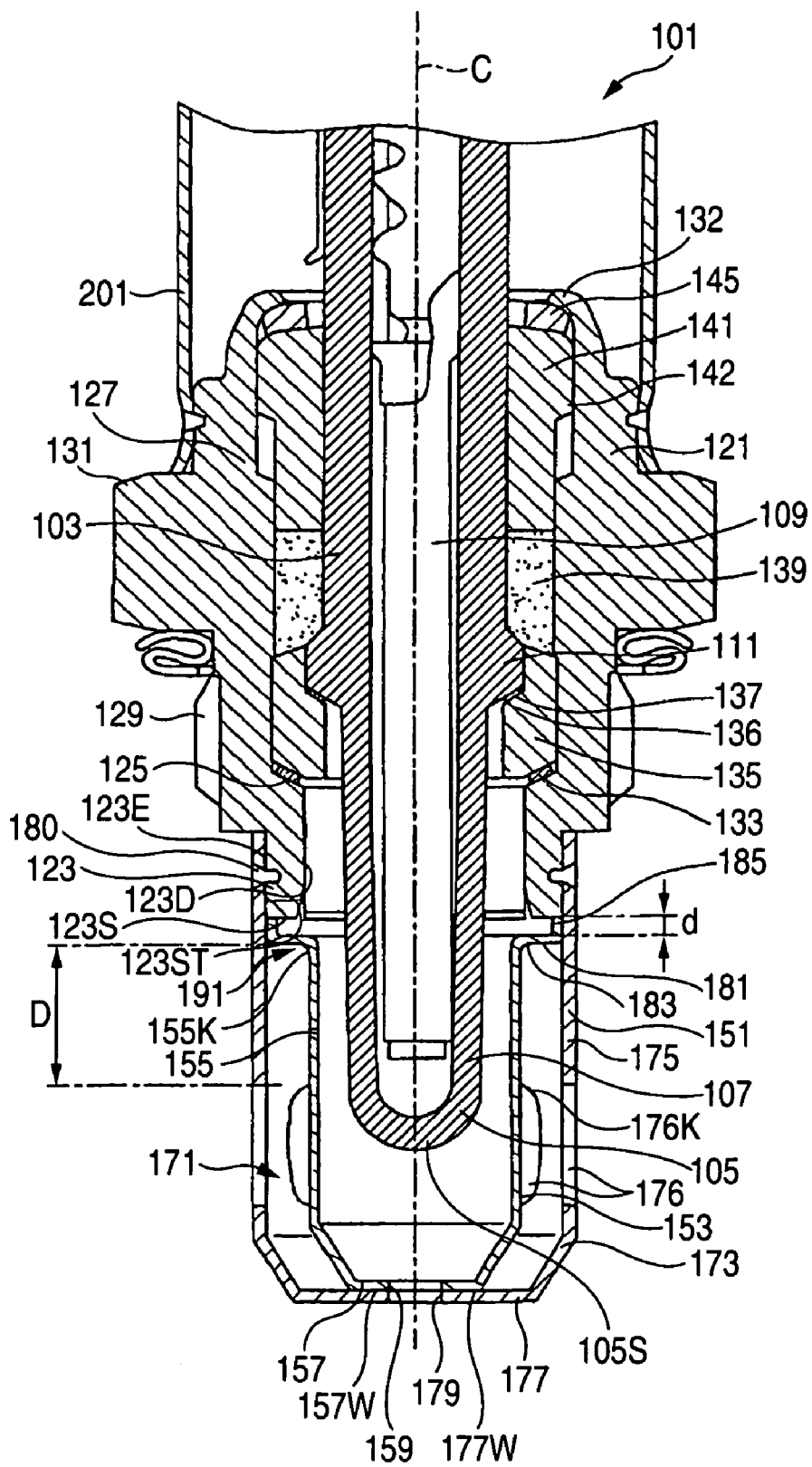
FIG. 3 is a sectional view of an essential portion of the gas sensor according to the embodiment.
Figure 4:
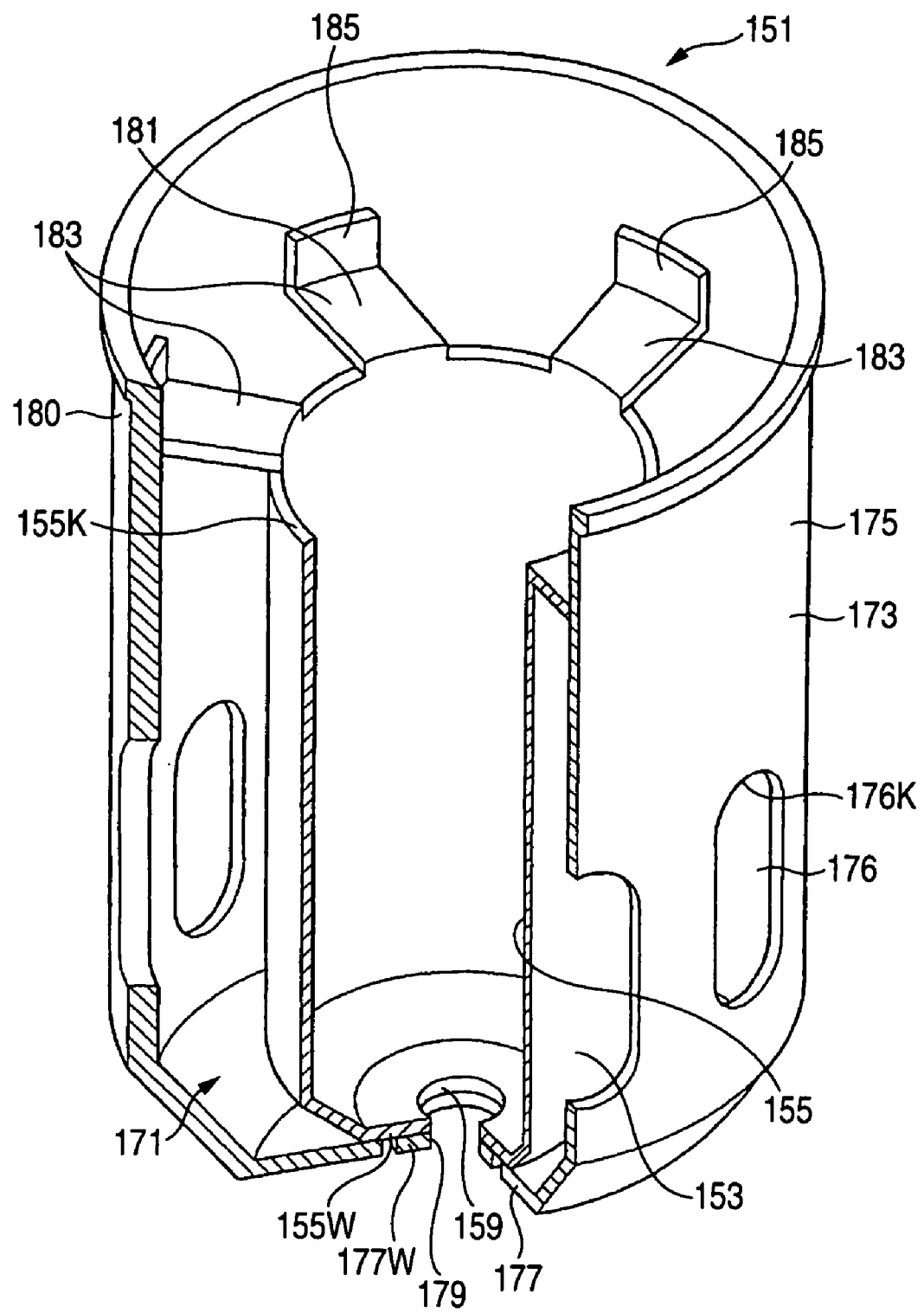
FIG. 4 is an explanatory view showing a protect of the gas sensor according to the embodiment.

A sectional view of a gas sensor 101 according to the embodiment is presented in FIG. 1; a top plan view of an essential portion is presented in FIG. 2, and a sectional view of the essential portion is presented in FIG. 3. Moreover, a protector 151 is shown in FIG. 4. Here in FIG. 1 to FIG. 4, the lower portion shows a leading end side, and the upper portion shows a trailing end side. This gas sensor 101 is an oxygen sensor, which is attached to the exhaust gas pipe of an internal combustion engine for measuring the oxygen concentration in the exhaust gas. The gas sensor 101 is provided with: a gas sensor element 103 extending in the direction of an axis C; a cylindrical metal shell 121 enclosing the gas sensor element 103; and the protector 151 covering such a leading end portion 105 of the gas sensor element 103 as will be exposed to the exhaust gas.

Of these, the gas sensor element 103 has gas sensing characteristics and is provided with a gas detecting portion 107, which is formed into a bottomed cylindrical shape having a closed leading end 105S and can measure the oxygen concentration in an object gas to be measured. In the inner side of this gas detecting portion 107, moreover, there is inserted a rod-shaped heater portion 109 for heating the gas detecting portion 107. The gas sensor element 103 is further provided near the axial center with a bulging portion 111, which bulges radially outward. This bulging portion 111 is utilized for holding the gas sensor element 103 in the metal shell 121.

The metal shell 121 is provided with a relatively thin leading end portion 123, which is inserted into the protector 151. The metal shell 121 is further provided on its inner circumference with a support portion 125 having such a support face 125, which is located at a position on the trailing end side of the leading end portion 123, as to hold (or support) the gas sensor element 103 in the axial direction. Moreover, a stepped portion 127 is formed on the trailing end side of the shelf portion 125. On the other hand, the metal shell 121 is provided on its outer circumference with a mounting threaded portion 129, which is located on the trailing end side of the leading end portion 123 for mounting the gas sensor 101 in the exhaust gas pipe. Moreover, the mounting threaded portion 129 is provided on its trailing end side with a hexagonal flange portion 131 (or a tool engaging portion), which is utilized when the gas sensor 101 is attached to the exhaust gas pipe.

This metal shell 121 holds the gas sensor element 103 so coaxially that the leading end portion 105 of the gas sensor element 103 protrudes from the leading end face of the metal shell 121. Specifically, a first leaf packing 133 is arranged on the shelf portion 125 of the metal shell 121. On the packing 133, there is further arranged a cylindrical first fixing member 135, which has a stepped portion on its inner circumference. The gas sensor element 103 is inserted through the first fixing member 135 so that its bulging portion 111 comes into engagement with the stepped portion 136 of the first fixing member 135 through a second leaf packing 137. On the trailing end side of the first fixing member 135, there is formed a filled sealing layer 139, which is filled with powder in the clearance defined by the outer circumference of the gas sensor element 103 and the inner circumference of the metal shell 121. On the trailing end side of the filled sealing layer 139, moreover, there is arranged a cylindrical second fixing member 141, which has a stepped portion 142 on its outer circumference and which admits the gas sensor element 103 therethrough on its inner side. On the trailing end side of the second fixing member 141, there is arranged an additionally fastened ring 145, which is additionally fastened by the trailing end portion 132 of the metal shell 121.

The protector 151 is made of a double structure, which has a cylindrical inner cover portion 153 for covering the leading end portion 105 of the gas sensor element 103 through a clearance and a cylindrical outer cover portion 173 arranged around the inner cover portion 153.

Of these, the outer cover portion 173 is made of a metallic material having a thickness of about 0.5 mm and is composed of an outer cylindrical portion 175 (having an external diameter of about 13.1 mm) and an outer bottom portion 177 located on the leading end side of the former. The outer cylindrical portion 175 is provided at its eight portions with outer gas introducing apertures 176, which can introduce the object gas from the outside into the inner side of the outer cover portion 175. The outer gas introducing apertures 176 individually have an elliptical shape and are arranged at an equal spacing in the circumferential direction and at positions on the leading end side from the center, as viewed in the axial direction. The outer bottom portion 177 is provided at its center with an outer leading end air vent hole 179 having a circular shape, which communicates with the outside in the leading end direction of the protector 151.

The inner cover portion 153 is made of a metallic material having a thickness of about 0.3 mm and is composed of an inner cylindrical portion 155 (having an external diameter of about 8.5 mm) and an inner bottom portion 157 located on the leading end side of the former. Unlike the outer cylindrical portion 175, the inner cylindrical portion 155 has no air vent hole. On the other hand, the inner bottom portion 157 is provided at its center with an inner leading end air vent hole 159 having a circular shape, which communicates with the outer leading end through hole 179 and which is connected to the outside in the leading end direction.

On the other hand, the inner cover portion 153 is provided with intermittent flange portions 183 (or elastic portions 181), which protrude at six portions radially outward from the trailing end 155K of the inner cylindrical portion 155 and which are arranged intermittently in the circumferential direction. As will be described hereinafter, those intermittent flange portions 183 can be so elastically deformed as are bent by the pushing force acting in the axial direction. Moreover, the intermittent flange portions 183 are provided at their radially outer side end portions with leg portions 185, which protrude individually toward the trailing end in the axial direction. Here, the ratio of the projected area, when projected from the axially leading end side of the intermittent flange portions 183 (i.e., the intermittent flange portions 183 in the elastically deformed state) to the open area of the outer gas introducing apertures 176 may be within a range of 5% to 40% and is set to about 22% in this embodiment.

In the inner cover portion 153 and the outer cover portion 173, the inner bottom portion 157 and the outer bottom portion 177 are fixed to each other by spot-welding them partially at four portions of the surrounding portion 157W of the inner leading end air vent hole 159 and the surrounding portion 177W of the outer leading end air vent hole 179. As a result, the inner leading end air vent hole 159 and the outer leading end air vent hole 179 communicate with each other. Moreover, the inner cylindrical portion 155 and the outer cylindrical portion 175 are so arranged that the side wall of the inner cylindrical portion 155 is located at a position to confront the outer gas introducing apertures 176 and that the inner cylindrical portion 155 and the outer cylindrical portion 175 are parallel to each other. Here, a clearance of about 0.1 mm is left between the outer bottom portion 157 and the outer bottom portion 177 excepting the four welded portions.

This protector 151 is so fixed that the trailing end portion 180 of the outer cover portion 173 (i.e., the trailing end portion of the outer cylindrical portion 175) is laser-welded to the outer circumference 123E of the leading end portion 123 of the metal shell 121. Moreover, the inner cover portion 153 is clamped in such a condition between the metal shell 121 and the outer cover portion 173 that the intermittent flange portions 183 (or the elastic portions 181) are elastically deformed in the pushing force in the axial direction. Specifically, the leading end portion (or the leading end face 123S) of the metal shell 121 pushes the leg portions 185 of the inner cover portion 153 toward the leading end side in the axial direction, and the outer bottom portion 177 of the outer cover portion 173 pushes the inner bottom portion 157 of the inner cover portion 153 toward the reside in the axial direction. As a result, the intermittent flange portions 183 are bent and elastically deformed.

On the other hand, the leading end portion 123 of the metal shell 121, the outer cylindrical portion 175 and the inner cylindrical portion 155 construct an inner gas introducing passage 191 for introducing the object gas introduced from the outer gas introducing apertures 176, into the clearance between the inner cover portion 153 and the leading end portion 105 of the gas sensor element 103. In this embodiment, the intermittent flange portions 183 are provided at their radially outer side end portions with the leg portions 185, which protrude toward the trailing end side in the axial direction thereby to allow the leading end face 123S of the metal shell 121 to abut against their own rear ends (or the trailing end face), so that the intermittent flanges 183 and the metal shell 121 are spaced to form the inner gas introducing passage 191. Therefore, this inner gas introducing passage 191 guides the object gas introduced from the outer gas introducing apertures 176, between the outer cylindrical portion 175 and the inner cylindrical portion 155 to the trailing end side. After this, the object gas is guided between the intermittent flange portions 183 and then over the trailing end 155K of the inner cylindrical portion 155 closer to the leading end side of the leading end portion 123 of the metal shell 121, as viewed in the axial direction, than the inner circumferential side end edge 123ST of the joining face (or the leading end face) joining an inner circumference 123D and the outer circumference 123E. Then, the object gas is guided into the clearance between the inner cover portion 153 and the leading end portion 105 of the gas sensor element 103 and is discharged through the inner leading end air vent hole 159 and the outer leading end air vent hole 179 to the outside of the protector 151.

Here in this embodiment, the distance d between the inner circumference end edge 123ST of the leading end portion 123 of the metal shell 121 and the trailing end 155K of the inner cylindrical portion 155 is set to about 0.8 mm, and the shortest distance in the axial direction between the trailing end 155K of the inner cylindrical portion 155 and the trailing end side edge 176K of the outer gas introducing apertures 176 is set to about 5.1 mm.

As shown in FIG. 1, a leading end portion 201S of a cylindrical metallic outer cylinder 201 is fixed from the outer side to the trailing end side of the hexagonal flange portion 131 of the metal shell 121 by the laser-welding method. Moreover, a grommet 203 made of rubber or the like is fitted and sealed by an additional fastening in a trailing end opening 201K of the metallic outer cylinder 201. At the center of the grommet 203, there is arranged a filter member 205 for introducing the atmosphere into the metallic outer cylinder 201 while preventing the infiltration of moisture. The grommet 203 is provided on its leading end side with a separator 207, which is made of insulating alumina ceramics. Moreover, sensor output lead wires 211 and 212 and heater lead wires 213 and 214 are arranged through the grommet 203 and the separator 207. Still moreover, the connector portions 215B and 215C of first and second sensor terminal fittings 215 and 216 and heater terminal fittings 217 and 218 are held in the separator 207 while being insulated from each other.

In the first sensor terminal fitting 215, the connector portion 215B grips and connects the sensor output lead wire 211 electrically, and the connector portion 215C is inserted into the bottomed hole of the gas detecting portion 107 and electrically connected with the in-sensor electrode layer. In the second sensor terminal fitting 216, moreover, the connector portion 216B grips and connects the sensor output lead wire 212 electrically, and the connector portion 216C grips the outer circumference near the trailing end of the gas detecting portion 107 and is electrically connected with the in-sensor electrode layer. On the other hand, the heater terminal fittings 217 and 218 are electrically connected with the heater lead wires 213 and 214, respectively, and are electrically connected with the electrode pads 109B and 109C of the heater portion 109, respectively.

Even if this gas sensor 101 is subjected to vibrations for a long term, the inner cover portion 153 is held in the clamped state between the leading end face 123S of the metal shell 121 and the outer bottom portion 177 of the outer cover portion 173 so that it is prevented from being violently vibrated in the outer cover portion 173. In addition, the elastic portions 181 are exemplified by the aforementioned intermittent flange portions 183 so that the protector 151 can be made of a simple structure while improving its vibration resistance. Moreover, the intermittent flange portions 183 are provided with the leg portions 185. Therefore, it is possible to construct such a communication passage (or the inner gas introducing passage 191) as can introduce the object gas between the intermittent flange portions 183 and over the trailing end 155K of the inner cylindrical portion 155 into the inner cover portion 153. On the other hand, the outer cover portion 173 and the inner cover portion 153 are welded at their leading end sides so that the vibration resistance of the protector 151 can be further improved.

Here, this gas sensor 101 can be manufactured by the well-known method. In this gas sensor 101, the protector 151 may be prepared by molding the inner cover portion 153 having the inner cylindrical portion 155, the inner bottom portion 157, the intermittent flange portions 183 and the leg portions 185, and the outer cover portion 173 having the outer cylindrical portion 175 and the outer bottom portion 177 separately and subsequently by fixing their leading end sides by the welding method. With these two cover portions 153 and 173 being fixed, the trailing end portion 180 of the outer cover portion 173 may be welded to the predetermined positions of the leading end portion 123 of the metal shell 121 while the intermittent flange portions 183 being elastically deformed by applying the leading end face 123S of the metal shell 121 to the trailing ends of the leg portions 185 of the inner cover portion 153.

Although the invention has been described in connection with its embodiment, the invention should not be limited to the aforementioned embodiment. It goes without saying that the invention can be suitably modified without departing from the gist thereof.

In the aforementioned embodiment, for example, the flange portions 183 are provided with the leg portions 185, against which the metal shell 121 is brought into abutment. In other words, the metal shell 121 abuts indirectly against the flange portions 183 or the elastic portions 181. However, the metal shell 121 may be brought into direct abutment against the flange portions 183 by omitting the leg portions 185. In this modification, it is difficult to construct the aforementioned inner gas introducing passage 191. Therefore, it is advisable to form the gas introducing apertures in the side wall of the inner cylindrical portion 155.

In the embodiment, moreover, the flange portions 183 protrude from the trailing end 155K of the inner cylindrical portion 155. In another mode, for example, the flange portions 183 may protrude from the axially intermediate portions of the inner cylindrical portion 155.

Moreover, the embodiment has exemplified the gas sensor element 103 having the bottomed cylindrical shape. However, the gas sensor element can have a plate shape.

In the embodiment, moreover, the outer gas introducing apertures 176 have the elliptical shape, and the inner leading end air vent hole 159 and the outer leading end air vent hole 179 have the circular shape. However, the shapes of those holes can be suitably modified into an elliptical or rectangular shape.

In the embodiment, moreover, the intermittent flange portions 183 protrude radially outward at the six portions. However, the number and shape of the intermittent flange portions should not be limited thereto but can be suitably modified.

This application is based on Japanese Patent application JP 2003-192263, filed Jul. 4, 2003, the entire content of which is hereby incorporated by reference, the same as if set forth at length.

What is claimed is:

1. A gas sensor comprising:
   a gas sensor element extending in an axial direction;
   a cylindrical metal shell enclosing said gas sensor element such that a leading end portion of said gas sensor element protrudes from its own leading end; and
   a protector fixed on said metal shell and covering said leading end portion of said gas sensor element,
   wherein said protector includes:
   a cylindrical outer cover portion fixed on said metal shell and having gas introducing apertures; and
   a cylindrical inner cover portion arranged on an inner side of said outer cover portion and having elastic portions being capable of being elastically deformed by a pushing force acting in an axial direction, the elastic portions being arranged on the inner side of said outer cover portion, and
   said inner cover portion is so clamped between said metal shell and said outer cover portion that said elastic portions are elastically deformed by said axial pushing force.

2. The gas sensor according to claim 1,
   wherein said inner cover portion includes an inner cylindrical portion enclosing said leading end portion of said gas sensor element, and
   said elastic portions include flange portions protruding radially outward from said inner cylindrical portion and elastically deformed when pushed toward a leading end side in an axial direction by said metal shell to come into direct or indirect abutment against said flange portions.

3. The gas sensor according to claim 2, wherein said flange portions are intermittent flange portions arranged intermittently in a circumferential direction.

4. The gas sensor according to claim 2, wherein said inner cover portion includes leg portions protruding from a radially outer end portions of said flange portions and positioned at their own trailing ends closer to a trailing end side than a trailing end of said inner cylindrical portion so that they are pushed toward a leading end side in an axial direction when a leading end of said metal shell comes into abutment against themselves.

5. The gas sensor according to claim 1, wherein at least part of said outer cover portion and at least part of said inner cover portion are fixed to each other.

6. The gas sensor according to claim 5, wherein said outer cover portion includes:
   an outer cylindrical portion fixed on said metal shell; and
   an outer bottom portion positioned closer to a leading end side than said outer cylindrical portion and having an outer leading end air vent hole,
   said inner cover portion includes:
   an inner cylindrical portion enclosing said leading end portion of said gas sensor element; and
   an inner bottom portion positioned closer to a leading end side than said inner cylindrical portion and having an inner leading end air vent hole communicating with said outer leading end air vent hole, and
   said outer bottom portion and said inner bottom portion are fixed to each other.

7. A gas sensor comprising:
   a gas sensor element extending in an axial direction;
   a cylindrical metal shell enclosing said gas sensor element such that a leading end portion of said gas sensor element protrudes from its own leading end; and
   a protector fixed on said metal shell and covering said leading end portion of said gas sensor element,
   wherein said protector includes:
   a cylindrical outer cover portion fixed on said metal shell and including
   an outer cylindrical portion fixed on said metal shell and having gas introducing apertures, and
   an outer bottom portion positioned on a leading end side of said outer cylindrical portion and having an outer leading end air vent hole communicating with an outside; and
   a cylindrical inner cover portion arranged on an inner side of said outer cover portion and including
   an inner cylindrical portion enclosing said leading end portion of said gas sensor element,
   an inner bottom portion positioned on a leading end side of said inner cylindrical portion and having an inner leading end air vent hole communicating with said outer leading end air vent hole of said outer cover portion,
   intermittent flange portions protruding radially outward from trailing ends of said inner cylindrical portion and arranged intermittently in a circumferential direction so that they are capable of being elastically deformed by a pushing force acting in an axial direction, the intermittent flange portions being arranged on the inner side of said outer cylindrical portion, and
   leg portions protruding toward a trailing end in an axial direction from radially outer end portions of said intermittent flange portions, and
   said intermittent flange portions are elastically deformed by pushing said leg portions of said inner cover portion toward a leading end in an axial direction with a leading end of said metal shell, and by pushing at least a portion of said inner bottom portion of said inner cover portion toward a trailing end in an axial direction with at least one portion of said outer bottom portion of said outer cover portion.

8. The gas sensor according to claim 1, wherein said inner cover portion comprises an inner cylindrical portion enclosing said leading end portion of said gas sensor element and leg portions protruding in the axial direction and parallel with the inner cylindrical portion, wherein said elastic portions comprise flange portions protruding radially outward from said inner cylindrical portion and integrally attaching to the leg portions, and wherein a surface of said leg portions abuts an inner surface of the cylindrical outer cover portion.

9. The gas sensor according to claim 7, wherein said intermittent flange portions and the metal shell are spaced by said leg portions to form an inner gas introducing passage.

* * * * *